United States Patent [19]

Danielson et al.

[11] Patent Number: 5,354,666
[45] Date of Patent: Oct. 11, 1994

[54] MAMMALIAN CELL LINE EXPRESSING BASEMENT MEMBRANE PROTEINS

[75] Inventors: Keith G. Danielson, Rosemont; Renato V. Iozzo, Villanova, both of Pa.

[73] Assignee: Thomas Jefferson University, Philadelphia, Pa.

[21] Appl. No.: 999,462

[22] Filed: Dec. 29, 1992

Related U.S. Application Data

[63] Continuation of Ser. No. 738,895, Aug. 1, 1991, abandoned.

[51] Int. Cl.$^5$ .......................... C12P 21/00; C12N 5/06
[52] U.S. Cl. ............................ 435/70.3; 435/240.2
[58] Field of Search ........... 435/240.2, 240.21, 240.23, 435/240.25, 240.22, 240.22, 240.243, 70.3

[56] References Cited

U.S. PATENT DOCUMENTS

| | | | |
|---|---|---|---|
| 4,808,532 | 2/1989 | Stampfer | 435/240.2 |
| 4,829,000 | 5/1989 | Kleinman et al. | 435/240.23 |
| 4,963,490 | 10/1990 | Churchouse et al. | 436/240.241 |
| 5,013,714 | 5/1991 | Lindstrom et al. | 514/4 |

OTHER PUBLICATIONS

Cook et al., *In Vitro Cell Dev. Biol.,* vol. 25, 1989, pp. 914–922.
Ledbetter et al., *J. Biol. Chem.* vol. 260, 1985, pp. 8106–8113.
Carlin et al., (1981) *J. Biol. Chem.* 256: 5209–5214.
Carlson et al., *J. Biol. Chem.,* 243:616–626 (1971).
Clark et al., (1987) *J. Biol. Chem.* 262: 10229–10238.
Hassell et al., (1980) *Proc. Natl. Acad. Sci. U.S.A.* 77: 4494–4498.
Iozzo et al., (1984) *J. Cell Biol.* 99: 403–417.
Iozzo et al., (1990) *J. Biol. Chem.* 265: 19980–19989.
Iozzo and Hassell, (1989) *Arch. Biochem Biophys.* 269: 239–249.
Kleinman, et al., (1982) *Biochemistry* 21: 6188–6193.
Laemmli et al., *Nature,* 227: 680–685 (1970).
Martinez-Hernandez et al., (1982) *Lab. Invest.* 47: 247–257.
Martinez-Hernandez et al., (1984) *Lab. Invest.* 51: 57–74.
Martinez-Hernandez et al., (1987) *Methods Enzymol.* 145: 78–103.
Morton, H. J., *In Vitro,* 6:89–108 (1970).
Orkin et al., (1977) *J. Exp. Med.* 145:204–220.
Paul, *Cell Tissue Culture,* 4th ed. (The Williams and Wilkins Co., Baltimore, Md. 1970).
Saito et al., (1968) *J. Biol. Chem.* 243: 1536–1542.
Saksela et al., (1988) *J. Cell. Biol.* 107:743–751.
Shively and Conrad, (1976) *Biochemistry* 15: 3932–2942.
Swarm et al., (1963) *J. Natl. Cancer Inst.* 31:953–974.
Timpl et al., (1979) *J. Biol. Chem.* 254: 9933–9937.
Timpl et al., (1983) *Eur. J. Biochem.* 137: 455–465.
Towbin et al., (1979) *Proc. Natl. Acad. Sci. U.S.A.* 76: 4350–4354.
Vigny et al., (1988) *J. Cell Biol.* 131:123–130.
Wasteson (1971) *J. Chromatogr.* 59: 87–97.
Wewer et al., (1985) *Differentiation* 30: 61–67.
Yang et al., (1980) *Proc. Natl. Acad. Sci. U.S.A.* 77: 2088–2092.
Yurchenco and Schittny, (1990) *FASEB J.,* 4:1577–1590.

*Primary Examiner*—Richard A. Schwartz
*Assistant Examiner*—James Ketter
*Attorney, Agent, or Firm*—Woodcock Washburn Kurtz Machiewicz & Norris

[57] ABSTRACT

EHS murine tumor cells express basement membrane proteins such as laminin, entactin, collagen and proteoglycan. An immortal mammalian cell line designated BAM having phenotypic characteristics of EHS murine tumor cells may be prepared by culture of EHS cells in nutrient culture medium supplemented with low concentration of mammalian serum. BAM cells express basement membrane proteins in vitro.

5 Claims, No Drawings

MAMMALIAN CELL LINE EXPRESSING BASEMENT MEMBRANE PROTEINS

This application is a continuation of application Ser. No. 738,895, filed Aug. 1, 1991, now abandoned.

FIELD OF THE INVENTION

This invention relates to a novel mammalian cell line which expresses basement membrane proteins and is phenotypically similar to EHS murine tumor cells useful for evaluation of matrix synthesis and biological effects of basement membranes.

BACKGROUND OF THE INVENTION

Basement membranes are highly specialized extracellular matrices which are strategically positioned between polarized epithelia and the thick collagenous mesenchyme. (Martinez-Hernandez, A., (1984) *Lab. Invest.*, 51: 57-74). In recent years it has been realized that basement membranes act not only as physical scaffolds and molecular filters but also as solid-phase regulators of a variety of cellular processes, including attachment, motility and differentiation (Yurchenco and Schittny, (1990) *FASEB J.*, 4:1577-1590). Basement membranes can also modulate cellular growth by acting as a reservoir for growth factors and by prolonging their in vivo half-life (Saksela, et al., (1988) *J. Cell. Biol.* 107:743-751; Vigny, et al. (1988) *J. Cell. Biol.* 131:123-130). The Englebreth-Holm-Swarm (EHS) murine tumor is a transplantable neoplasm; (Swarm, et al., (1963) *J. Natl. Cancer Inst.* 31:953-974); that has been very useful to the scientific community primarily because of its intrinsic ability to synthesized and deposit large amounts of basement membrane constituents (Orkin, et al., (1977) *J. Exp. Med.* 145:204-220). Tissue extracts of EHS tumor contain laminin (Timpl, et al. (1979) *J. Biol. Chem.* 254: 9933-9937), type IV collagen (Kleinman, et al., (1982) *Biochemistry* 21: 6188-6193), a high-$M_r$ heparin sulfate proteoglycan (Hassell, et al. (1980) *Proc. Natl. Acad. Sci. U.S.A.* 77: 4494-4498), and entactin/nidogen (Carlin, et al. (1981) *J. Biol. Chem.* 256: 5209-5214); (Timpl, et al. (1983) *Eur. J. Biochem.* 137: 455-465), four gene products characteristic of basement membrane matrices (Martinez-Hernandez (1987) *Methods Enzymol.* 145: 78-103). Although primary cultures of EHS tumor cells have been previously maintained for up to 1 week (Ledbetter, et al. (1985) *J. Biol. Chem.* 260: 8106-8113), no continuous cell line has been yet established from the EHS tumor. The lack of an EHS-derived cell line has precluded a number of metabolic studies, such as long-term labelling and detailed turnover analysis of various basement membrane macromolecules. Therefore, there is a long-felt need for a phenotypically stable mammalian cell line from the EHS tumor.

OBJECTS OF THE INVENTION

It is a principal object of the invention to provide a novel continuous or immortalized mammalian cell line having the phenotype of EHS murine tumor cells.

It is a further object of the present invention to provide a method of preparing said novel mammalian cell line.

It is still a further object of the present invention to provide a method of producing basement membrane proteins in vitro.

It is yet a further object of the present invention to provide a method of propagating difficult cells.

These and other objects of this invention will become apparent from review of the instant specifications.

SUMMARY OF THE INVENTION

The usefulness of EHS tumor resides in its ability to synthesize and deposit a pericellular matrix enriched with the main structural components of basement membrane (Orkin, et al. (1977) *J. Exp. Med.* 145: 204-220). Although short-term cultures of EHS tumor cells have been utilized previously (Ledbetter, et al. (1985) *J. Biol. Chem.* 260: 8106-8113); Wever, et al., (1985) *Differentiation* 30: 61-67), no continuous or immortalized EHS-derived cell line has yet been established. This has hampered progress on understanding the regulatory mechanisms involved in the synthesis, cellular expression and turnover of basement membrane constituents. In accordance with the present invention, a continuous cell line, designated "BAM", to indicate that it is a basement membrane protein producing cell line, has been established from the murine EHS tumor. BAM cells have been subcultured for over 40 passages and have maintained phenotypic and biological properties of the parent EHS tumor cells. BAM cells have retained an epithelioid morphology and the ability to induce EHS-like tumors in mice. Biochemical and immunochemical studies demonstrate that BAM cells synthesize laminin A and B chains, collagen type IV, entactin and basement membrane specific heparin sulfate proteoglycan. These cells assemble a basement membrane, in vitro.

In one embodiment of the present invention a BAM cell line is established from EHS tumor tissue. EHS murine tumor fragments were implanted into mice. Thereafter, tumor fragments were removed and minced. Explants were seeded into flasks containing supplemented nutrient culture medium having a low concentration of mammalian serum and incubated at about 35° C. to about 38° C. Cells were later passaged. Within a few months, the growth medium was simplified. The BAM cell line eliminates the need for animals in which to maintain basement membrane expressing cells. Using BAM cells, large quantities of cells can be grown in vitro. Large scale cell culture would be less costly than techniques employing animals and would eliminate contamination of EHS type cells by other cell types.

In a further embodiment of the present invention a method of propagating difficult cells is provided. BAM cells may be cultured for a period of time sufficient for deposit of basement membrane protein matrices. Thereafter BAM cells may be removed from the culture and difficult cells may be propagated on basement membrane protein coated culture dishes or other vessels in which cells may be cultured.

The production of basement membrane proteins in vitro will facilitate the study of cell attachment, cell adhesion, cell migration, cyto-differentiation and other cellular processes to which basement membrane proteins may be found to be integrally related.

DETAILED DESCRIPTION OF THE INVENTION

In accordance with the present invention, a method of preparing a continuous or immortalized mammalian cell line expressing the phenotype of EHS murine tumor cells is provided.

EHS murine tumors are generally maintained by subcutaneous implantation of tumor fragments into mice such as BALB and C57/BL mouse strains. A primary cell culture of the present invention may be initiated by seeding explants of EHS tumor tissue which has been removed from mice. Explants may be incubated in any growth medium which provides sufficient supplements to encourage, for example, cell growth, cell proliferation and other desirous features known to those skilled in the art. These conventional culture media, described for example by H. J. Morton, *In Vitro*, 6:89–108 (1970) contain known essential amino acids, mineral salts, vitamins and carbohydrates. In preferred embodiments of the present invention, primary cultures are incubated in a medium comprised of Dulbecco's Modified Eagle's medium and Ham's/F-12 medium supplemented with low concentration of fetal bovine serum, and insulin, transferrin, sodium selenite, phosphoethanolamine, ethanolamine, epidermal growth factor, bovine pituitary extract, serum extender and gentamicin sulfate. In some preferred embodiments of the present invention, culture medium is supplemented with from about 1% to about 5% fetal bovine serum. In still more preferred embodiments of the present invention, from about 1% to about 2% fetal bovine serum may supplement culture medium. From about 3 to about 7µg/ml each of insulin and transferrin is preferably added to supplement culture medium of the present invention. In addition, from about 3 to about 7 ng/ml of sodium selenite may preferably be added to said culture medium. From about 300 to about 400 ng/ml of phosphoethanolamine and about 100 to about 200 ng/ml of ethanolamine may also be added to the culture medium. From about 5 to about 15 ng/ml of each of epidermal growth factor and gentamicin sulfate may also preferably be added to culture medium of the present invention. Cultures may be incubated in environments conducive to cell attachment, growth and proliferation known to those skilled in the art and by reference to well known texts on cell culture such as, for example, Paul, *Cell Tissue Culture*, 4th ed. (The Williams and Wilkins Co., Baltimore, Md. 1970). In one embodiment of the present invention primary cultures may be incubated at 37° C. in a humidified atmosphere containing 3% $CO_2$.

Passage of confluent cells may be performed about 50 days to about 70 days after initiation of primary cultures. In preferred embodiments of the present invention passage may be performed about 60 days after initiation of primary cultures. Thereafter, and preferably within a few months, growth medium may be simplified. In preferred embodiments of the present invention cells are maintained in a simplified medium having low mammalian serum concentration. Preferably mammalian serum concentration is maintained at from about 1% to about 5%.

A continuous or immortalized mammalian cell line prepared as described above is encompassed by the present invention. The said cell line, referred to hereinafter as BAM cell line, appears cuboidal with prominent nucleoli in vitro. Ultrastructural analysis of BAM cells cultured for two weeks on collagen gels showed pleomorphic epithelial-like cells with coarse chromatin, prominent nucleoli and abundant rough endoplasmic reticulum. BAM cells contain poorly developed functional complexes and abundant extracellular matrix. In addition, BAM cells show relative polarization with a basal portion and an apical portion containing a few microvilli. BAM cells do not contain mycoplasma.

Cells of the present invention exhibit at confluency a saturation density of from about $1 \times 10^4$/cm$^2$ to about $1 \times 10^5$/cm$^2$. In preferred embodiments of the present invention cells exhibited a saturation density of $7 \times 10^4$/cm$^2$. At saturation density cells of the present invention become more rounded and refractile. Multilayering of the cells is not seen.

BAM cell populations double in from about 15 hours to about 24 hours when grown in DMEM/F-12 medium supplemented with low concentrations of mammalian serum. In some embodiments of the present invention doubling occurs at about 20 hours. BAM cell growth is inhibited slightly by serum concentrations greater than about 10% and therefore population doubling may occur at different rates depending upon serum concentration.

BAM cells may also be maintained in serum free medium containing insulin, transferrin, and selenium. Testing of growth factors may be accomplished in such a serum free medium.

Karyotype analysis indicated that BAM cell line of the present invention is aneuploid containing 49–50 chromosomes. A large marker chromosome is present.

While the EHS tumor originally arose in the ST/EH mouse strain, it can be successfully passaged in C57/BL and BALB/c mice. BAM cells injected intramuscularly into BALB/c mice induced tumors exhibiting identical morphology to the original EHS tumor. Latency periods may range from about 1 to about 15 months.

At the interface between BAM cells cytoplasm becomes flattened and clear basement membrane is deposited. The basement membrane deposited has a relatively constant thickness of about 1 µm. Pockets of basement membrane-like material may be observed in areas between cells as well as in dilated rough endoplasmic reticulum.

BAM cells express a number of basement membrane components. These components include laminin A and B, entactin, collagen type IV, and basement membrane specific heparin sulfate proteoglycan. In particular, BAM cells are of interest due to unusually high expression of collagen type IV. BAM cells may express significant amounts of collagen type IV. Type IV polypeptides can be seen after staining with coumassie blue and can be detected by Western blot.

Electrophoresis of delipidated BAM cell pellets resulted in a major protein band migrating at about 220 kDa (where laminin B1 and B2 chains migrate). In addition, a number of high $M_r$-proteins in the range of collagen type IV (170 kDa–185 kDa) and nidogen/entactin (150 kDa) were observed. Western blot and immunoprecipitation affirmed these findings.

The cell surface of BAM cells contain numerous proteoglycan granules. These proteoglycan granules may also be found in the extracellular matrix deposits between cells and in extracellular matrix deposits which occur at the basal portion between BAM cells and collagen gel upon which the BAM cells may be grown. Proteoglycan granules deposited by BAM cells range in size but generally are about 30 nm in diameter.

A major proteoglycan synthesized by BAM cells of the present invention contain about 80% heparin sulfate chains of 25–34 kDa and about 20% chondroitin sulfate chains of 12–17 kDa. The molecule in comprised of an about 400–450KDa protein core to which about 2–3 heparin sulfate chains and about one chondroitin sulfate chain are covalently attached.

In further embodiments of the present invention the production of basement membrane matrices is achieved in vitro. BAM cells may be cultured under conditions favorable to cellular expression of basement membrane proteins, such as those described above. Cultures may be maintained until sufficient basement membrane matrix is deposited. Thereafter, cells may be removed from the vessels in which they were growing, for example, culture dishes or flasks. Removal may be accomplished by scraping or treatment with strong base such as ammonium hydroxide followed by aspiration or any other methods known to those skilled in the art which is in keeping with the present invention. Various means can be used to separate and purify basement membrane protein containing fractions from cells and cell culture products. These various recovery means include the known techniques for the separation and purification of proteinaceous substances in general such as, for example, dialysis, salt and solvent precipitation, adsorption with gels, cellulose ion exchange, chromatography, Sephadex gel filtration, electrophoresis, lyophilization and other procedures known to those skilled in the art.

In other embodiments of the present invention, basement membrane matrix may be produced and recovered intact. BAM cells of the present invention may be cultured in culture dishes. Cell cultures may be maintained as described above until a coating of basement membrane matrix is deposited. Thereupon, BAM cells may be extracted from the culture dishes by, for example, treatment with strong base such as ammonium hydroxide followed by aspiration. Treatment with strong base followed by careful washes with, for example, saline solution, may also be sufficient to remove cells from culture dishes, while leaving the matrix intact. Cell culture plates prepared in this manner may be useful, for example, for propagation of difficult cells. By difficult cells, it is meant cells which require more than standard culture technique for growth in cultures. Neuronal cells, smooth muscle cells, epithelial cells and hepatocytes are examples of difficult cells. Cell cultures may be maintained as described above until a coating of basement membrane matrix is deposited which is sufficient to support propagation of cells of interest. Thereupon, BAM cells may be extracted from the culture dishes in a manner by which the protein matrix remains intact, as described above. Such procedures should occur in an aseptic environment so that contamination of cells of interest is avoided. Cells of interest may then be plated in basement membrane protein-coated culture dishes under conditions amenable to cells of interest, known to those skilled in the art. The following examples are illustrative but are not meant as limiting of the present invention.

EXAMPLES

EXAMPLE 1

Establishment of a Cell Line (BAM) from EHS Tumor Tissue and Induction of Yumors in Mice The murine EHS tumor was maintained by intramuscular implantation of tumor fragments into the hind limbs of C57/BL or BALB/c mice. For initiation of primary cell cultures, tumor fragments were removed aseptically and minced finely with apposed scalpels. Explants were seeded into 25 cm$^2$ flasks containing 2 ml of growth medium consisting of 1:1 (V:V) Dulbecco's Modified Eagle's medium and Ham's F-12 medium (DMEM/F-12) which was supplemented with the following components: 2% fetal bovine serum (FBS), insulin (5 $\mu$g/ml), transferrin (5 $\mu$g/ml), sodium selenite (5 ng/ml), phosphoethanolamine (350 ng/ml), ethanolamine (150 ng/ml), epidermal growth factor (EGF, 10 ng/ml), bovine pituitary extract (BPE, 10 ug/ml), Mito+ serum extender (1:5 dilution) from Collaborative Research (Bedford, Mass.), and gentamicin sulfate (10 ug/ml). The flasks were incubated undisturbed for 48 hrs at 37° C. in a humidified atmosphere containing 3% $CO_2$ to allow the explants to attach. After 45 days, cellular division was observed and after 60 days enough cells were available for cryopreservation. Confluent cultures were subsequently passaged by removal of cells with 2.4 mg/ml dispase (Grade II, Boerhringer Mannheim Biochemicals, Indianapolis, Ind.), in Puck's saline A. Within a few months, the growth medium was simplified to include DMEM/F-12 supplemented with 1% FBS, Mito+ serum extender (1:1), and BPE (5 ug/ml). Currently, the cells are grown in DMEM/F-12 (1:1) containing 2% FBS and gentamicin sulfate (10 ug/ml) and are passaged using trypsin (125 mg/ml) and EDTA (0.5 mM) to dissociate the cell monolayer. To date, this cell line, designated BAM to indicate derivation from a tumor producing basement membrane material, has been maintained successfully for over 2 years and for approximately 40 continuous passages.

For induction of tumors in mice, 50 ul-aliquots of DMEM/F-12 containing approximately $4 \times 10^6$ BAM cells was injected intramuscularly into the hind limb of each BALB/c mouse. Injections were performed with BAM cells at both early (10th) and late (26th) passages. Tumors (1 cm diameter) were removed and fixed in Bouin's solution for histology or frozen for further analysis.

EXAMPLE 2

Culture of Cells Within Collagen Gels and Morphological Studies

BAM cells were grown as multicellular spheroids within collagen (Type I) gels to detect synthesis of basement membrane-like structures. To prepare collagen gels, the method of Yang, et al. (1980) *Proc. Natl. Acad. Sci. U.S.A.* 77: 2088–2092), was used with slight modifications. The gel was comprised of rat tail collagen solution (1.6 mg/ml in 0.1% acetic acid), Medium 199 (8X), and 0.34 N NAOH at a ratio of 82:12:6 (V/V). The solution (0.5 ml/dish) was overlayed in each 35 mm diameter well of a 6-well cluster plate and allowed to gel at 37° C. BAM cells were allowed to attach to this substratum overnight and then an additional 1.15 ml neutralized collagen mixture was overlayed on top of the cells. After the collagen had solidified, approximately 2 ml of growth medium was added to the culture. Sodium ascorbate (50 $\mu$g/ml) was added daily to the growth medium. For light microscopy BAM cells or tissue fragments of EHS tumor, either primary or induced by BAM cells, were fixed in Bouin's fixative overnight and processed for histology using standard techniques (Iozzo, et al. (1984) *J. Cell Biol.* 99: 403–417). For electron microscopy, BAM cells were cultured for 2 weeks in collagen gels and then processed in the presence or absence of 0.2% ruthenium red (Iozzo, et al. 1984).

EXAMPLE 3

Immunohistochemistry

For immunohistochemical studies BAM cells were grown on collagen type I-coated Tissue-Tek slide chambers. At subconfluency, the cells were washed with PBS (X3), and fixed in acetone for 15 minutes at 4° C. Polyclonal antibodies elicited against laminin from ED-PYS carcinoma (Martinez-Hernandez, et al. (1982) *Lab. Invest.* 47: 247-257), or against EHS collagen Type IV and heparin sulfate proteoglycan (Hassell et al., (1980) *Proc. Natl. Acad. Sci. U.S.A.* 77: 4494-4498) were used. The monospecificity of these antibodies has been defined by Western blotting and electron microscopic immunohistochemistry (Martinez-Hernandez, et al. (1982) *Lab. Invest.* 47: 247-257; Martinez-Hernandez, et al. (1984) *Lab. Invest.* 51: 57-74). Normal rabbit serum was used as control. Cells were stained according to previously described procedures (Martinez-Hernandez, et al. (1987) *Methods Enzymol.* 145: 78-103). Briefly, cultures were sequentially incubated with normal goat serum, primary antibodies, biotinylated goat anti-rabbit IgG, and peroxidase-streptavidin complex. The peroxidase reaction was developed with $H_2O_2$ and diaminobenzidine. The cells were subsequently dehydrated in graded ethanols and mounted with Permount.

EXAMPLE 4

Extraction of Cell/Matrix Proteins, Electrophoresis and Western Blotting

Subconfluent cells in either T-75 flasks or 60 mm dishes were cultured for 1 week in the presence or absence of 50 ug/ml ascorbic acid, freshly added every day. Cells were twice washed with serum-free medium and scraped in 10 ml of methanol. The bottom of the culture was again scraped with additional 10 ml of methanol and combined with the cell extract. The 10,000 g delipidated pellet was resuspended in 250-400 ul of Laemmli, et al., *Nature*, 227:680-685 (1970) buffer containing 100 mM DTT, boiled for 5 minutes and analyzed on 5%, 6.5% or 5-12.5% gradient NaDodecylsulfate polyacrylamide gel electrophoresis (SDS-PAGE). The [$^{35}$S]methionine-labeled samples were processed for fluorography as described in Iozzo et al. (1990) *J. Biol. Chem.* 265: 19980-19989. Western blotting was performed as described in Towbin et al. (1979) *Proc. Natl. Acad. Sci. U.S.A.* 76: 4350-4354, and reacted with monospecific antibodies against laminin and collagen type IV.

EXAMPLE 5

Immunoprecipitation of Laminin and Entactin Synthesized by BAM Cells

A confluent culture of BAM cells grown in a 35 mm dish was washed three times with Hanks' balanced salt solution (HBSS) and depleted of methionine by incubation for 25 min in DMEM lacking methionine and FBS. Cells were metabolically labeled for 30 min with 1 ml of the same medium containing 1 mCi [$^{35}$S]methionine (1000 Ci/mmol) (ICN Biochemicals, Irvine, Calif.). Extraction of cell/matrix and immunoprecipitation with antibodies against laminin and entactin was performed as described in Ledbetter et al. (1985) *J. Biol. Chem.* 260: 8106-8113. The immunoprecipitates were resolved on SDS-PAGE under reducing conditions and visualized by fluorography (Iozzo and Hassell (1989) *Arch. Biochem Biophys.* 269: 239-249).

EXAMPLE 6

Characterization of Proteoglycans Synthesized by BAM Cells

Confluent cultures were labeled for 24 hours with carrier-free [$^{35}$S]sulfate, 40-50 µCi/ml (45 Ci/mg sulfur). The medium and cell/matrix fractions were processed separately. Briefly, the cell/matrix was extracted with 4 M guanidine HCl, 2% Triton X-100, containing several protease inhibitors (Iozzo, et al. (1984) *J. Cell Biol.* 99:403-417), and purified by sequential Sephadex G-50, DEAE-Trisacryl and Sepharose CL-4B chromatography (Iozzo, et al. (1990) *J. Biol. Chem.* 265: 19980-19989 and references therein). Glycosaminoglycans were released by alkali borohydride treatment (Carlson, et al., *J. Biol. Chem.*, 243:616-626 (1971) and subjected to nitrous acid treatment at low pH (Shively and Conrad, (1976) *Biochemistry* 15: 3932-2942) and chondroitinase ABC or AC digestion (Saito et al., (1968) *J. Biol. Chem.* 243: 1536-1542). The size of glycosaminoglycan chains eluting from Sepharose CL-6B was calculated according to Wasteson (1971) *J. Chromatogr.* 59: 87-97. For characterization of the protein core, [$^{35}$S]sulfate-labeled samples were digested with protease-free chondroitinase ABC (EC 4.2.2.4) for 1 hour or with heparitinase for 30 minutes or sequentially with both enzymes. Samples were dried under vacuum, resuspended in Laemmli buffer and analyzed by SDS-PAGE and fluorography. Radiolabeled proteoglycan samples were also analyzed on 1% agarose gels followed by autoradiography (Iozzo et al, (1990) *J. Biol. Chem.* 265: 19980-19989).

EXAMPLE 7

Establishment of Cell Line from EHS Tumor: Growth Conditions and Induction of Tumors in Mice BAM cells in vitro appeared cuboidal with prominent nucleoli. At confluency, the cells exhibited a saturation density of $7 \times 10^4/cm^2$, with some cells becoming more rounded and refractile. However, multilayering of the cells was not seen. Occasional giant cells were present. A population doubling of 20 hours was characteristically observed for BAM cells grown in DMEM/F-12 supplemented with relatively low concentrations (2%) of mammalian serum. High serum concentrations (e.g., 10%) did not improve growth, but was found to inhibit growth slightly. The BAM cell line could be maintained for over a month in serum-free medium containing insulin, transferrin, and selenium, thus allowing the possibility to test a number of growth factors. The BAM cell line was tested for mycoplasma and found to be negative for this microorganism. Karyotypic analysis indicated that this cell line was aneuploid containing 49-50 chromosomes per cell. A large marker chromosome was present. The EHS tumor originally arose in the ST/EH mouse strain but was successfully passaged in C57/BL and BALB/c mice. After injection of BAM cells intramuscularly into BALB/c mice, tumors exhibiting identical morphology to the original EHS tumor arose after variable latency periods ranging from 2 months to 14 months.

EXAMPLE 8

Morphology and Immunohistochemistry of BAM Cells

Following 26 continuous passages, BAM cells exhibited an overall morphology similar to the original cells cultured for only 10 passages. The appearance of the mouse tumors induced by injection of BAM cells grown for either 10 or 26 consecutive passages was similar to the original EHS tumor. The BAM cells synthesized a significant amount of extracellular matrix in vitro, as shown by the pericellular deposition of PAS-positive material. A similar, though more pronounced deposition of PAS-positive material could be observed in the sections of tumor induced by BAM cells. The ability to synthesize and deposits basement membrane glycoproteins and proteoglycans was maintained during subsequent in vitro subculturing. BAM cells at passage 37, in fact, reacted intensely with antibodies against collagen type IV, laminin, and basement membrane heparin sulfate proteoglycan.

EXAMPLE 9

Ultrastructural Studies of BAM Cells cultured on collagen type I gel

Ultrastructural analysis of BAM cells cultured for two weeks on collagen gels showed pleomorphic epithelial-like cells with coarse chromatin, prominent nucleoli and abundant rough endoplasmic reticulum. The cells contained poorly-developed junctional complexes and abundant extracellular matrix. BAM cells showed a relative polarization, with a basal portion and an apical portion containing a few microvilli. The cytoplasm of BAM cells became quite flattened at the interface between the cells and the collagen gel, with deposition of a clear basement membrane. This thin membrane had a relatively constant thickness of 1 μm. Pockets of basement membrane-like material could be observed in areas between cells as well as in dilated rough endoplasmic reticulum. Following processing of a parallel sample with ruthenium red, a cationic dye that binds proteoglycans and reveals them as electron dense granules, the cell surface of BAM cells contained numerous proteoglycan granules. Also, the extracellular matrix deposits between cells and those assembled at the basal portion, between BAM cells and the collagen gel, contained the same-size granules. The average diameter of the granules was about 30 nm. The presence of a similar ruthenium red granules at both the cell surface and the basement membrane suggests that there might be only one single proteoglycan species synthesized by the BAM cells. Taken together, these results show that BAM cells synthesize a matrix that resembles basement membrane both at the immunological and ultrastructural level.

EXAMPLE 10

Biosynthesis of Laminin, Collagen Type IV and Entactin

Where aliquots of delipidated cell pellets, either unlabeled or metabolically labelled with [$^{35}$S]methionine, for 24 hours were electrophoresed on a 6.5% SDS-PAGE, a major protein band migrating at about 220 kDa (where laminin B1 and B2 chains migrate) was observed. In addition, a number of high $M_r$-proteins in the range of collagen type IV (170–185 kDa) and nidogen/entactin (150 kDa) were noted. Western blot analysis revealed the presence of laminin and of collagen type IV polypeptides. As expected, ascorbate treatment increased the levels of collagen type IV, but had no appreciable effect on the levels of laminin.

BAM cells were pulsed for 30 minutes with [$^{35}$S]methionine and the newly synthesized polypeptides were immunoprecipitated from the cell/matrix extract using monospecific antibodies against laminin (A and B chains) and entactin. Immunoprecipitates were separated on a 5% SDS-PAGE under reducing conditions. The results clearly showed that BAM cells synthesize relatively high levels of both laminin A and B chains. Resolution of laminin B1 and B2 chains was achieved by running the sample on a 6.5% SDS-PAGE for longer periods. In contrast, the pre-immune serum showed no immunoreactivity. The expected 150 kDa protein could be also immunoprecipitated from the same experiment using an antiserum against entactin; in contrast, preimmune serum lacked this band.

EXAMPLE 11

Characterization of Proteoglycans Synthesized by BAM Cells

Confluent cultures were labeled for 24 hours with [$^{35}$S]sulfate and the proteoglycan purified by sequential Sephadex G-50, DEAE-Trisacryl and Sepharose CL-4B chromatography. The cell/matrix fraction contained two major peaks, designated C-I and C-II, eluting at about 0.3 and 0.4 M NaCl, respectively. The less charged pool C-I contained primarily small glycopeptides with $K_{av}$ of 0.8 on Sepharose CL-4B, while 10% of 35S activity eluted as a broad polydispersed peak of larger $M_r$. In contrast, the more charged pool C-II contained a major proteoglycan with a $K_{av}$ of 0.38 (C-IIa) and a glycopeptide peak with $K_{av}$ of 0.68 (C-IIb). Alkaline borohydride treatment of purified pool C-I gave glycosaminoglycan chains of about 12 kDa, with a smaller proportion of chains being of about 25 kDa. In contrast, pool C-IIa contained chains of about 25 kDa, while pool C-IIb gave chains of about 17 kDa. The C-IIa glycosaminoglycans were treated with nitrous acid or with chondroitinase ABC or AC. The results showed that about 80% of the labeled glycosaminoglycans were degraded by $HNO_2$ at low pH, and that the resistant material became a discrete peak of about 12 kDa, smaller than the total intact chains. Further digestion with chondroitinase ABC or AC established that the smaller chains were composed of chondroitin sulfate. Similar results were obtained with the purified pool C-I. These findings indicate that the major proteoglycan synthesized by BAM cells contain about 80% heparin sulfate chains of about 25 kDa and 20% chondroitin sulfate chains of 12–17 kDa.

The medium fraction contained a single polydispersed peak eluting at about 0.38 M NaCl from DEAE-Trisacryl. This pooled material gave two major peaks on Sepharose CL-4B, with $K_{av}$ of 0.25 and 0.51 (Ma and Mb), respectively, larger than the two corresponding samples C-IIa and C-IIb from the cell/matrix fractions. Interestingly, both Ma and Mb peak contained glycosaminoglycan chains of identical size ($M_r$ - 34 kDa), but larger than those observed in the cell associated proteoglycan C-IIa. Chondroitinase ABC digestion degraded about 20% of the chains without altering the elution position of the resistant chains. In contrast, nitrous acid degraded about 80% of the chains and the resistant chains were now of about 18 kDa. Chondroitinase AC, followed by nitrous acid treatment, completely degraded the chains (not shown), indicating that the 18 kDa chains were chondroitin sulfate. Similar results were also obtained with the Mb pool. Taken together, these results indicate that the secreted proteoglycan has an overall composition similar to the proteoglycan associated with the cell/matrix fractions but it contains longer heparin sulfate chains. This may also explain the larger hydrodynamic size of Ma proteoglycan as judged by Sepharose CL-4B chromatography.

EXAMPLE 12

Electrophoresis of Proteoglycans and Analysis of the Protein Core

To investigate further the nature of the cell/matrix and medium proteoglycans, aliquots of the various pools isolated as above were analyzed by 5% SDS-PAGE or 1% agarose gel electrophoresis. Pool C-I contained only a small proportion of the radioactivity on top of the gel while the majority of the radioactivity was not retained in the gel. This is in agreement with the Sepharose CL-4B studies and indicate that most of pool C-I is composed of small glycopeptides. Agarose gel electrophoresis of C-I also confirmed the low-$M_r$ nature of this material. Similarly, the presence of free chains in pool Mb was confirmed by both SDS-PAGE and agarose gel electrophoresis. In contrast, pools C-II and Ma contained primarily high $M_r$-material that barely penetrated the 5% SDS-PAGE. When analyzed by 1% agarose gel electrophoresis, C-IIa and Ma fractions comprised a polydispersed proteoglycan band. This proteoglycan migrated significantly faster than the major cartilage proteoglycan isolated from chick chondrocytes, but before the 400 kDa cartilage underglycosylated proteoglycan induced by DON (Clark et al., (1987) J. Biol. Chem. 262: 10229–10238).

The studies indicated that one single hybrid proteoglycan with a $M_r$ 500–600 kDa could contain both heparin and chondroitin sulfate chains. Alternatively, the chains could be linked to two distinct but co-migrating protein cores. To investigate this question, purified Ma proteoglycan was digested with chondroitinase ABC, heparitinase or with both enzymes and subjected to SDS-PAGE and fluorography. The results showed that while chondroitinase ABC did not have any significant effect of the mobility of the proteoglycan, heparitinase allowed the penetration of the radiolabeled Ma proteoglycan in the upper portion of the gel. Sequential digestion with chondroitinase ABC and heparitinase allowed the further migration of Ma proteoglycan within the 5% separating gel, just above the 400 kDa marker. No additional lower-$M_r$ core proteins were detectable even after longer exposures of the autoradiograms.

Collectively, these results indicate that BAM cells synthesize a major hybrid proteoglycan containing a 400–450 kDa protein core to which 2–3 heparin sulfate chains of 25–34 kDa and one chondroitin sulfate chain of about 17 kDa are covalently attached.

What is claimed is:

1. A process for producing basement membrane proteins in vitro comprising growing immortalized EHS murine tumor cells in nutrient culture medium wherein said culture medium is Dulbecco's modification of Eagle's minimum essential medium supplemented with 1% to 5% mammalian serum, 3 to 7 µg/ml insulin, 3 to 7 µg/ml transferrin, 3 to 7 ng/ml sodium selenite, 300 to 400 ng/ml phosphoethanolamine, 100 to 200 ng/ml ethanolamine, 5 to 15 ng/ml epidermal growth factor, and 5 to 15 µg/ml gentamicin sulfate for a sufficient time to allow for deposit of basement membrane proteins in extracellular matrices; and isolating the resulting basement membrane proteins from the cells or cell product.

2. A method of propagating difficult cells comprising:
   a) growing immortalized EHS murine tumor cells in culture vessels containing nutrient culture medium supplemented with 1% to 5% mammalian serum, 3 to 7 µg/ml insulin, 3 to 7 µg/ml transferrin, 3 to 7 ng/ml sodium selenite, 300 to 400 ng/ml phosphoethanolamine, 100 to 200 ng/ml ethanolamine, 5 to 15 ng/ml epidermal growth factor, and 5 to 15 µg/ml gentamicin sulfate for a sufficient time for deposit of basement membrane proteins in extracellular matrices in said culture vessels;
   b) removing said immortalized EHS murine tumor cells from said culture vessels and
   c) adding difficult cells to said culture vessels in which basement membrane proteins have been deposited in step a).

3. A process for obtaining an immortalized basement membrane producing cell line which comprises incubating EHS tumor explants in nutrient culture medium supplemented with 1% to 5% mammalian serum, 3 to 7 µg/ml insulin, 3 to 7 µg/ml transferrin, 3 to 7 ng/ml sodium selenite, 300 to 400 ng/ml phosphoethanolamine, 100 to 200 ng/ml ethanolamine, 5 to 15 ng/ml epidermal growth factor, and 5 to 15 µg/ml gentamicin sulfate, for a sufficient time to reach confluency.

4. An immortalized EHS cell line which expresses laminin, collagen type IV, entactin and basement membrane specific heparan sulfate proteoglycan.

5. The immortalized EHS cell line of claim 4 wherein said laminin comprises laminin A, laminin B1 and laminin B2.

* * * * *